(12) United States Patent
Lehmann (10) Patent No.: US 7,211,069 B2
(45) Date of Patent: May 1, 2007

(54) NEEDLE COVER AND CANNULA SUPPORT COMPRISING A NEEDLE COVER

(75) Inventor: Hans-Ulrich Lehmann, Bellmund (CH)

(73) Assignee: TecPharma Licensing AG, Burgdorf (CH)

( * ) Notice: Subject to any disclaimer, the term of this patent is extended or adjusted under 35 U.S.C. 154(b) by 396 days.

(21) Appl. No.: 10/358,622

(22) Filed: Feb. 5, 2003

(65) Prior Publication Data

US 2003/0149404 A1 Aug. 7, 2003

(30) Foreign Application Priority Data

Feb. 6, 2002 (DE) ................................ 102 04 836

(51) Int. Cl.
*A61M 5/32* (2006.01)
(52) U.S. Cl. ..................................... 604/198
(58) Field of Classification Search ................ 604/110, 604/263, 192, 198, 197, 164.08, 181, 187; 128/919
See application file for complete search history.

(56) References Cited

U.S. PATENT DOCUMENTS

| | | | | |
|---|---|---|---|---|
| 4,790,828 A | * | 12/1988 | Dombrowski et al. | 604/198 |
| 4,867,172 A | * | 9/1989 | Haber et al. | 600/576 |
| 4,898,589 A | * | 2/1990 | Dolgin et al. | 604/198 |
| 4,904,244 A | * | 2/1990 | Harsh et al. | 604/187 |
| 4,911,706 A | * | 3/1990 | Levitt | 604/198 |
| 4,935,013 A | * | 6/1990 | Haber et al. | 604/192 |
| 4,950,250 A | * | 8/1990 | Haber et al. | 604/192 |
| 5,078,697 A | * | 1/1992 | Rammler | 604/198 |
| 5,108,379 A | * | 4/1992 | Dolgin et al. | 604/198 |
| 5,246,427 A | * | 9/1993 | Sturman et al. | 604/192 |
| 5,250,031 A | * | 10/1993 | Kaplan et al. | 604/110 |
| 5,295,972 A | * | 3/1994 | Mischenko | 604/192 |
| 5,304,137 A | * | 4/1994 | Fluke | 604/110 |
| 5,531,704 A | * | 7/1996 | Knotek | 604/192 |
| 5,630,803 A | * | 5/1997 | Tamaro | 604/263 |
| 5,688,241 A | * | 11/1997 | Asbaghi | 604/110 |
| 5,951,525 A | * | 9/1999 | Thorne et al. | 604/198 |

(Continued)

FOREIGN PATENT DOCUMENTS

EP 0344606 A2 12/1989

(Continued)

*Primary Examiner*—Nicholas Lucchesi
*Assistant Examiner*—Theodore J. Stigell
(74) *Attorney, Agent, or Firm*—Dorsey & Whitney LLP; David E. Bruhn (57) ABSTRACT

A needle cover for covering an injection needle of an injection device, such as an injection pen, including a cover which can be shifted longitudinally along the longitudinal axis of the needle and which covers a proximal end of the needle in a needle protecting position, a restoring means for axially returning the cover from a retracted position towards the proximal end of the needle into an advanced position, and a latch for preventing the cover from being retracted in the needle protecting position, wherein the position of the cover is different in the advanced position and in the needle protecting position, and the latch is activated to prevent the cover from being retracted when the cover is shifted near to the needle protecting position. The present invention encompasses a cannula support comprising such a needle cover, wherein the needle cover is detachably or non-detachably connected to the cannula support.

29 Claims, 7 Drawing Sheets

U.S. PATENT DOCUMENTS

| | | | |
|---|---|---|---|
| 6,409,706 B1* | 6/2002 | Loy | 604/198 |
| 6,719,731 B2* | 4/2004 | Parmigiani | 604/192 |
| 6,986,759 B1* | 1/2006 | Jeremijevic | 604/198 |
| 2001/0053892 A1* | 12/2001 | Parmigiani | 604/197 |

FOREIGN PATENT DOCUMENTS

| | | |
|---|---|---|
| IT | EP 1163919 A2 * | 12/2001 |
| WO | WO 99/59660 | 11/1999 |

* cited by examiner

NEEDLE COVER AND CANNULA SUPPORT COMPRISING A NEEDLE COVER

PRIORITY CLAIM

This utility patent application claims the priority of German Patent Application No. 102 04 836.3, filed on Feb. 6, 2002, which is incorporated in its entirety by reference.

BACKGROUND

The present invention relates to a needle cover for covering an injection needle of an injection device and to a cannula support comprising such a needle cover. The needle cover is preferably used in injection pens for administering a medicine, for example insulin or hormone, or for injecting another therapeutic or diagnostic fluid.

Non-covered injection needles involve a significant risk of injury and infection. Suitable securing elements are therefore required, to securely cover at least the tips of the needles. Certain injection devices require official admission as medical devices because they comprise an integrated medicine container, for example a replaceable ampoule. In order that such medical devices can be used repeatedly, it is advantageous for reasons of hygiene if the injection needle itself can be easily replaced, for example by plugging a cannula support comprising the injection needle onto the injection device. Thus, there is a need for reliable and cost-effective needle covers.

Another pending patent application by the Applicant discloses a needle cover for an injection pen. Said cover comprises a cylindrical sleeve surrounding the needle and serving as a covering means which may be longitudinally shifted in the axial direction of the needle. A spring acting on the covering means serves as a restoring means which proximally advances the needle cover after the device has been used once. Latching means latch in the proximal end position and prevent the needle cover from being retracted again for another needle injection.

This needle cover is comparatively costly because it comprises a comparatively large number of components, is comparatively large and has to be fixed to the injection device itself.

SUMMARY

It is an object of the present invention to provide a cost-effective needle cover which is easy to handle and effectively prevents pricking injuries from injection needles. Furthermore, a cannula support is to be provided comprising such a needle cover.

This object is addressed by a needle cover comprising the features of a covering means which can be shifted longitudinally along the axial length of the needle and which covers a proximal end of the needle in a needle protecting position, a restoring means for axially returning the covering means from a retracted position towards the proximal end of the needle into an advanced position, and a latching means for preventing the covering means from being retracted in the needle protecting position, wherein the position of the covering means is different in the advanced position than in the needle protecting position, and the latching means is activated to prevent the covering means from being retracted when the covering means is shifted near to the needle protecting position. In some embodiments, the objects are addressed by providing a cannula support comprising such a needle cover.

In one embodiment, the present invention comprises a needle cover for covering an injection needle, comprising a cover which can be moved along the needle and which covers a proximal end of said needle in a needle protecting position, a return mechanism for axially moving said cover from a retracted position toward said proximal end of the needle into an advanced position, and a latch for preventing the cover from being retracted in said needle protecting position, wherein the position of the cover is different in said advanced position than in the needle protecting position, and the latch is activated to prevent the cover from being retracted when the cover is moved near the needle protecting position.

In accordance with the invention, the position of the covering means is different in the advanced position and in the needle protecting position and the latching means is activated when the covering means is shifted near the needle protecting position, to prevent the covering means from being retracted. As long as the latching means has not yet been activated, the covering means can therefore be advanced and retracted unhindered. In the latched needle protecting position, by contrast, the danger of pricking injuries is effectively prevented.

In one embodiment, the restoring means preferably assumes its resting position in the advanced position, such that restoring forces always return the covering means to the advanced position, as long as the latching means has not yet been activated. In the advanced position, the proximal end of the needle preferably protrudes out of the covering means. In accordance with one variant, however, the proximal end of the needle can already be covered by the covering means in the advanced position, to prevent any unintentional pricking injuries.

In accordance with one preferred embodiment, the restoring means includes flexible elements which project symmetrically from the covering means in the manner of flexible side bows and extend substantially in the longitudinal direction of the needle. Arranging them symmetrically offers the advantage that pressing the side bows together results in the covering means being axially, longitudinally shifted and not laterally adjusted. For even better guiding, the covering means is linearly guided on the injection needle, for example via a bore in the covering means, said bore surrounding the injection needle and thus guiding the covering means when it is shifted.

The covering means may also serve as a support element to which there is unrestricted access from the proximal end, for resting on the tissue when the injection needle is injected into the tissue. Injecting the injection needle can be effectively assisted by suitably shaping the support element.

In one preferred embodiment, the latching means comprises means respectively projecting from facing sides of the elastic side bows. Said latching means can for example be formed as spring-elastic elements comprising a snapping element and, in the latched needle protecting position, can grip behind an edge of an opposing, flexible side bow. In some embodiments, each of the snapping elements preferably comprises a chamfer which the edge of the opposing, flexible element slides along when the latching means latches. Thus, the latching means is automatically activated when the covering means is advanced, immediately before the covering means reaches the needle protecting position.

The spring-elastic elements may be provided on diametrically opposing facing sides of the spring-elastic side bows, such that the snapping elements can only be unlatched again by comparatively awkward gripping. Thus, the latching of the needle protecting position is effectively prevented from being unintentionally released.

In accordance with another embodiment, the covering means includes at least two telescopic sleeves surrounding the needle. In accordance with one variant, the proximal sleeve can be connected to the spring-elastic side bows. In accordance with another variant, no spring-elastic side bows need to be provided. In this embodiment, the latching means is designed such that the sleeves can be latched beyond the advanced position by being relatively rotated or axially shifted relative to each other. To this end, the latching means can include a coulisse guide on a side wall of a sleeve or on a proximal circumferential rim of a distal sleeve, said coulisse guide guiding the relative rotation in order to transfer the sleeves into the needle protecting position, or the latching means can include locking elements which lock into each other when a proximal sleeve is axially shifted into the needle protecting position.

Alternatively, a bellow can serve as the covering means, simultaneously possessing the restoring forces to return it to the advanced position.

BRIEF DESCRIPTION OF THE DRAWINGS

The invention will now be described by way of examples and by referring to the accompanying drawings.

FIG. 4, including

In the figures, identical reference numerals indicate identical or functionally identical elements and functional groups.

DETAILED DESCRIPTION

Figure 1:
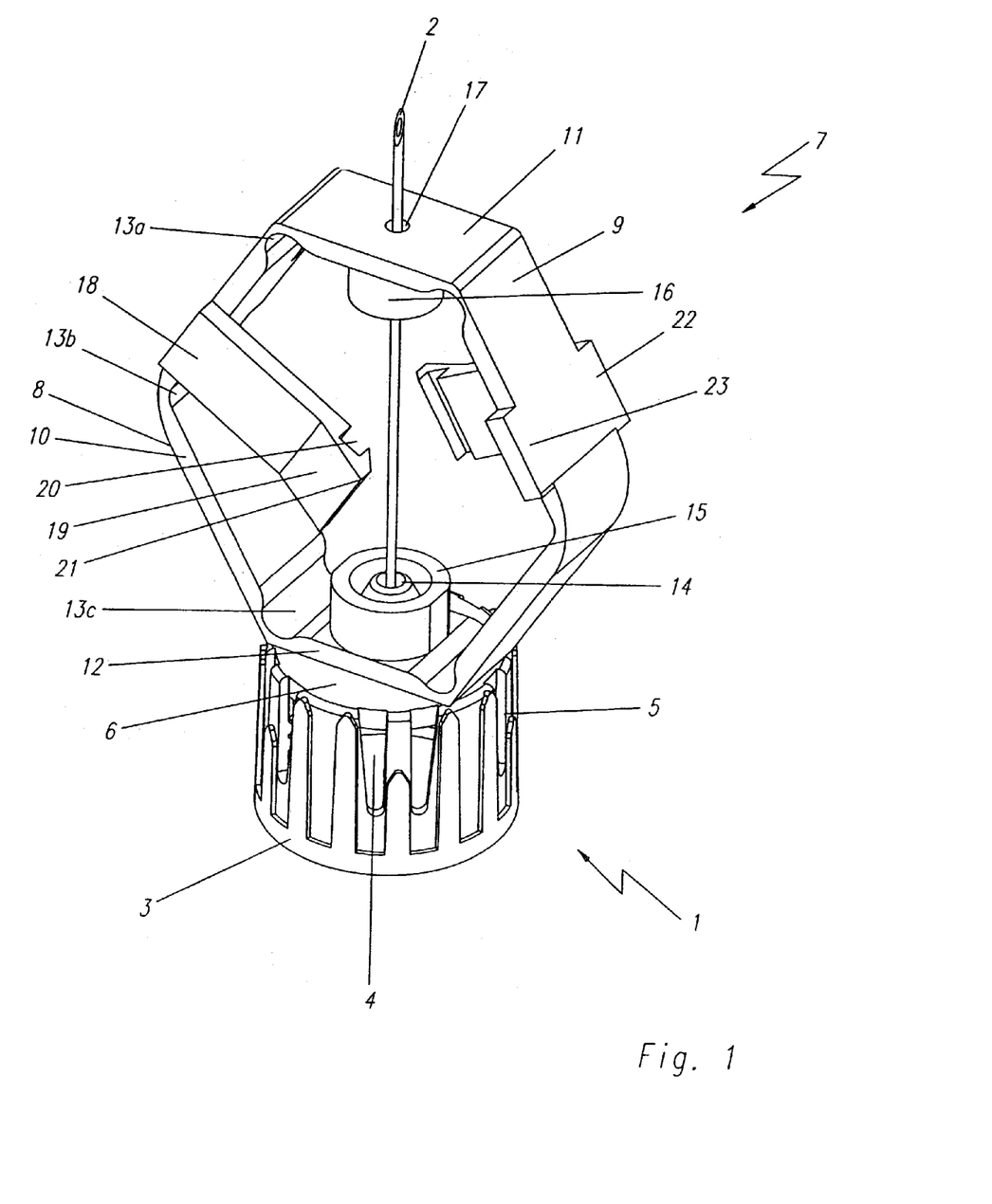
FIG. 1 depicts a cannula support comprising a needle cover in accordance with the present invention, in an advanced position.

FIG. 1 shows a cannula support 1 comprising a needle cover 7 in accordance with the invention, in an advanced position. The cannula support 1 comprises a cylindrical side wall 3 and a base 6. The cannula support 1 can be connected to an injection device, preferably an injection pen, or to an adapter for an injection device. When plugging the cannula support 1 onto the injection device (not shown), the distal end of the injection needle 2 punctures a septum or a membrane of a container for a medicine or for another therapeutic or diagnostic fluid.

The cannula support 1 comprises suitable connection means for mechanically connecting it to the injection device or the adapter. As shown in FIG. 1, locking elements 5 are formed on the inner wall of the cannula support 1, said elements meshing with an outer thread or with corresponding locking elements on the injection device or adapter. The cylindrical side wall 3 comprises a plurality of longitudinal slits 4 for expanding the cannula support 1 when it is plugged onto the injection device.

The needle cover 7 can be fixedly connected to the cannula support 1 by means of suitable connecting techniques, such as for example ultrasound welding, melting, pressing, adhering or the like. The needle cover 7 can also be connected detachably to the cannula support 1, to which end snapping elements or other suitable connecting elements can be provided on the needle cover 7, which mesh with corresponding snapping elements or connecting elements on the cannula support 1.

As shown in FIG. 1, the needle cover 7 comprises two symmetrically arranged side bows 8 which represent elastic elements and generate an elastic restoring force in order to return the side bows to the advanced position I shown in FIG. 1 in which the side bows 8 assume their resting position.

As shown in FIG. 1, the needle cover 7 exhibits a substantially hexagonal shape in the advanced position, comprising: a base plate 12 connected to the base 6 of the cannula support 1; an opposing support element 11 extending substantially parallel to the base plate 12, said element 11 representing a covering means and serving as a support facing side when the needle 2 is injected into the tissue; and two upper parts 9 and two lower parts 10 which together form a side bow 8 in each case.

In the transition region to the support element 11, the upper parts 9 comprise weak points 13a. In the transition region to the base plate 12, the lower parts 10 comprise weak points 13c. In the connecting region between the upper part 9 and the lower part 10, a weak point 13b is provided in each case, at substantially half the height of the needle cover 7. Thus, when the support element 11 is longitudinally shifted, the needle cover 7 is substantially deformed only in the region of the weak points 13a–c, without the side areas 9, 10, 11, 12 of the needle cover 7 being deformed.

In its cross-section, the needle cover 7 is formed point-symmetrically with respect to the needle 2, such that forces acting in the longitudinal direction of the needle 2 or forces acting on the side areas 9, 10 of the needle cover 7 result in the needle cover 7 being symmetrically compressed or stretched and thus in the needle 2 being shifted in its longitudinal direction. Instead of the two side bows 8 shown, the needle cover 7 can also comprise more side bows.

At the proximal end, i.e., the front end, of the needle cover 7, the support element 11 comprises a bore 17 and a cylindrical receptacle 16 which surrounds the proximal end of the needle 2. At the distal end, the needle cover 7 comprises a cylindrical sleeve 15 which surrounds the needle 2 and the cannula base 14. The cylindrical sleeve 15 serves as a stopper for the cylindrical receptacle 16 and limits the shifting of the support element 11 together with the receptacle 16 in the distal direction, in the retracted position shown in FIG. 2.

Figure 3:
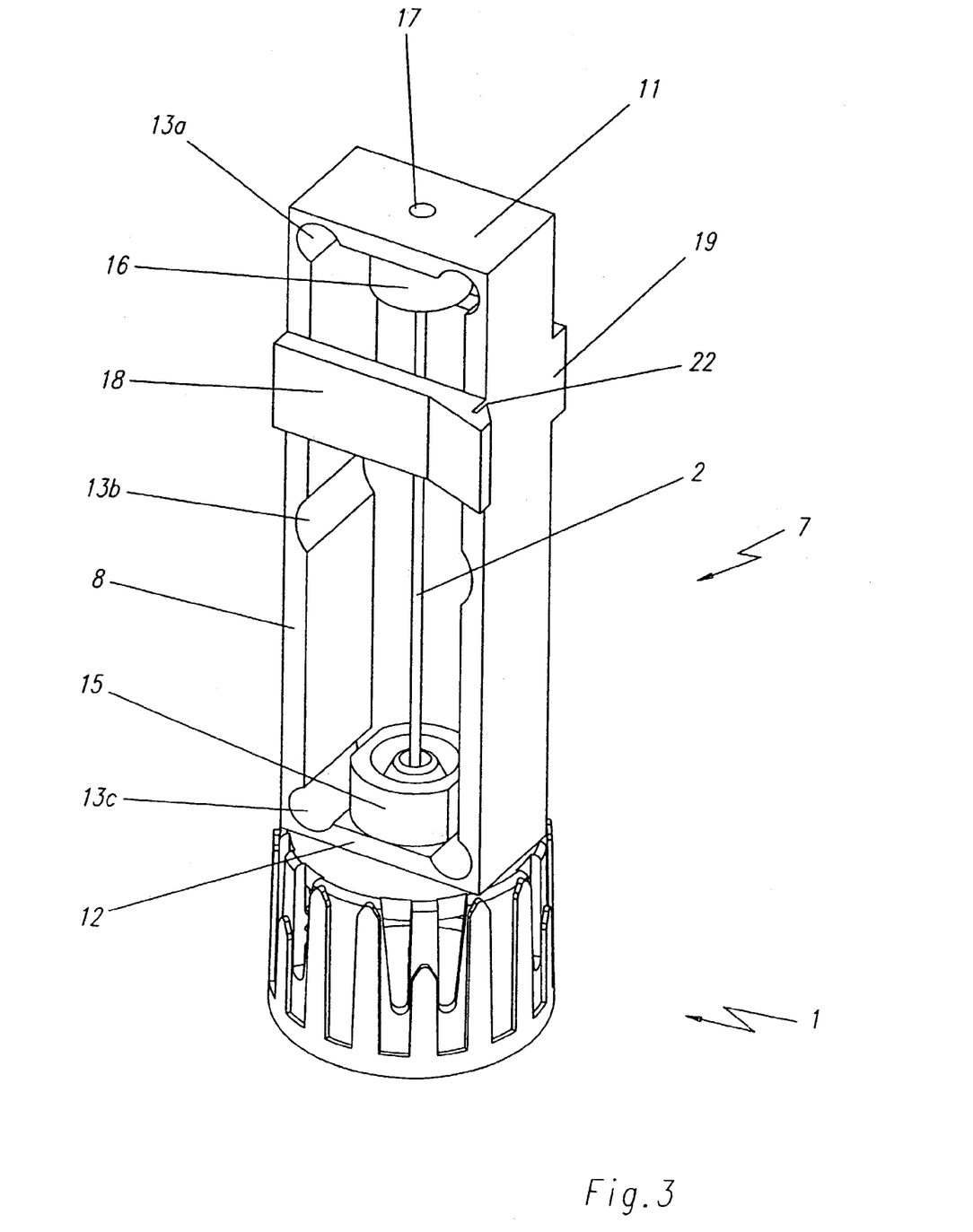
FIG. 3 depicts a cannula support comprising a needle cover, in a latched needle protecting position.

The support element 11 together with the receptacle 16 serves as a covering means for covering the needle in the latched needle protecting position shown in FIG. 3. The support element 11 is linearly guided on the needle 2 by the bore 17 and the cylindrical receptacle 16.

A spring-elastic bow 18 and a transverse beam opposite are respectively positioned on the facing sides of the upper parts 9. The bow 18 projects substantially vertically from the upper part 9 to the inner space of the needle cover 7, such that in any axial position of the needle cover 7, the support element 11 is freely accessible from the proximal end, to serve as a support area as the needle 2 is injected into the tissue.

The bow 18 ends in a snapping element 19 serving as a latching means and comprising a longitudinal groove 20 and a chamfer 21 on its front facing side. In the latched needle protecting position shown in FIG. 3, the transverse beam 22 meshes with the longitudinal groove 20 of the snapping element 19 and an outer edge 23 of the opposing transverse beam 22 grips behind the snapping element 19.

Figure 2:
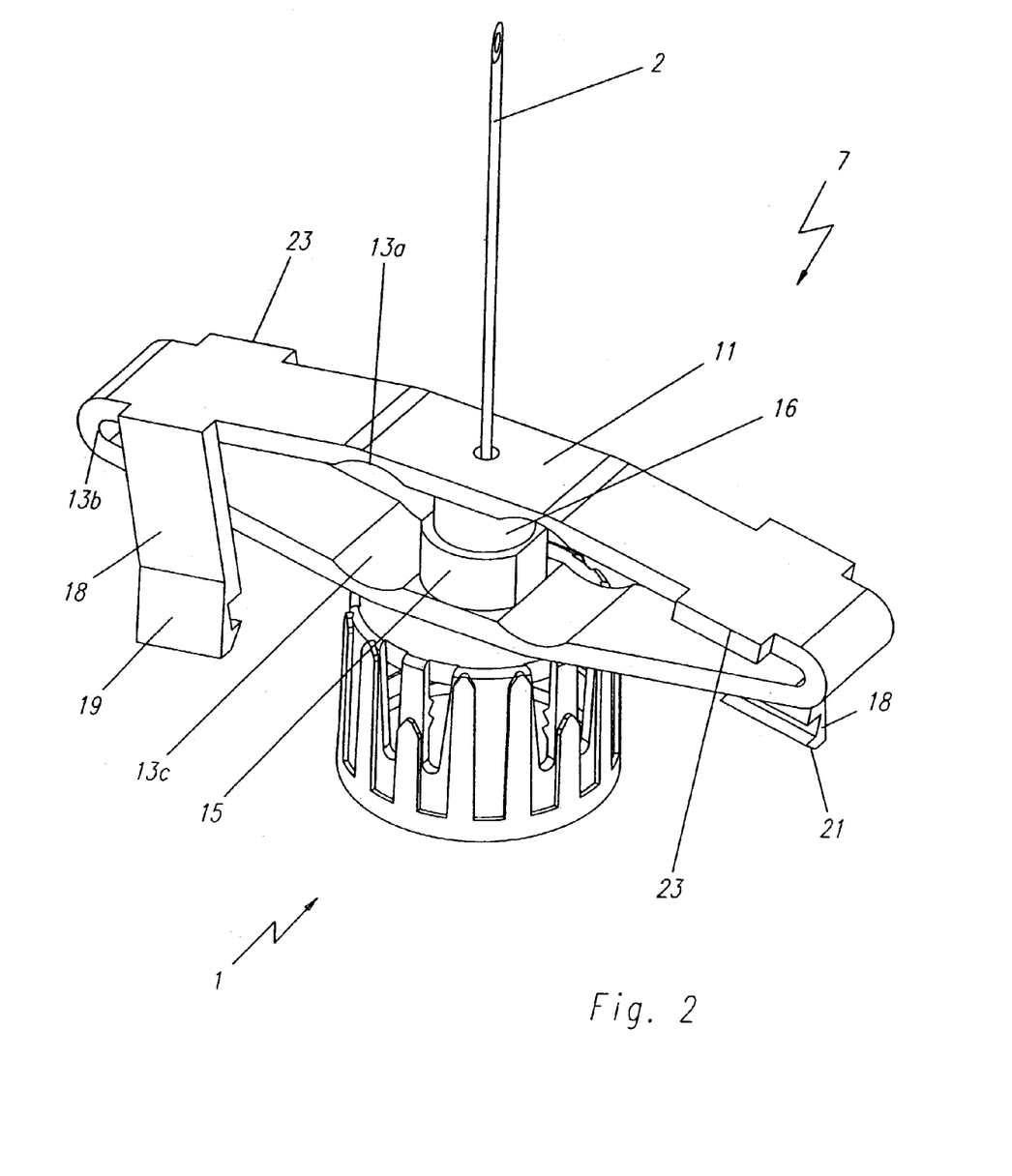
FIG. 2 depicts a cannula support comprising a needle cover in accordance with the present invention, in a retracted position.

As shown in FIGS. 2 and 3, the bows 18 and the transverse beams 22 are respectively arranged on diametrically opposing facing sides of the side bows 8. The length of the bows 18 with the snapping element 19 is designed such that the latching means only latches near the proximally foremost position of the support element 11. Also, the support element 11 together with the needle receptacle 16 can be freely shifted in the axial direction of the needle 2.

The needle cover 7 is made of a flexible material, for example plastic, and is designed such that the resting position of the restoring means is the advanced position shown in FIG. 1 in which the support element 11 and/or the needle receptacle 16 is situated in the vicinity of the proximal end of the needle 2. In this advanced position, the proximal end of the needle 2 can protrude proximally beyond the support element 11, as shown in FIG. 1. Alternatively, the proximal end of the needle 2 can also not protrude beyond the extension of the upper parts 9 in the direction of the longitudinal axis of the needle 2, such that the needle cover 7 can also be securely gripped from the proximal end using two fingers, without any danger of inadvertently touching the needle 2. In this alternative embodiment, the proximal end of the needle—with the needle cover in the advanced or resting position—can also be positioned inside the needle receptacle 16, in which case the axial length of the needle receptacle 16 is designed such that the proximal end of the needle is also positioned inside the needle receptacle 16 in the latched needle protecting position shown in FIG. 3.

Thus, by applying a force to the support element 11 in the direction of the distal end of the needle 2, the needle cover 7 can be retracted from the advanced position into the retracted position shown in FIG. 2. In this position, the needle cover 7 substantially exhibits a rhombic profile. Since the spring-elastic bows 18, with the snapping element 19, are respectively arranged on the facing side of the upper part 9, the bow 18 protrudes towards the distal end of the needle 2, such that the support element 11 is freely accessible. The support element 11 thus serves as a stopper up to which the injection needle 2 can be injected into the tissue. A suitably shaped attachment can be provided on the proximal side of the support element 11, to pre-set the injection angle of the needle 2 into the tissue. If, for example, a wedge-shaped attachment is provided on the element 11, then the injection needle is injected into the tissue at an angle pre-set by the angle of the wedge.

In the retracted position, the weak points 13a and 13c are maximally expanded and the weak points 13b are maximally compressed together. When the injection needle 2 is removed from the tissue, the restoring forces cause the needle cover 7 to be returned to the advanced resting position shown in FIG. 1.

In order to transfer the needle cover 7 to the latched needle protecting position shown in FIG. 3, a force is exerted on the needle cover 7, preferably in the region of the weak points 13b, i.e., approximately at half the height of the needle cover, by pressing the side areas 9 or 10 together. If the resulting, proximally acting adjusting force exceeds the restoring force of the side bows 8 serving as the restoring means, then the support element 11 together with the needle receptacle 16 is shifted in the longitudinal direction of the needle, towards the proximal end of the needle. When the support element 11 is advanced, the side walls 9, 10 of the needle cover 7 are distended and the snapping element 19 increasingly approaches the opposing transverse beam 22.

Lastly, the chamfer 21 of the snapping element 19 abuts the inner edge of the transverse beam 22. If the side walls 9, 10 of the needle cover are moved further together, the inner edge of the transverse beam 22 slides along the chamfer 21, such that the spring-elastic bow 18 is pressed outwards, out of the plane formed by the facing sides of the side bows 8. If the needle cover 7 is pressed further together, the vertex of the chamfer 21 eventually reaches the outer edge 23 of the opposing transverse beam 22, such that the spring-elastic bow 18 snaps back, due to its restoring force, into its initial position in which the transverse beam 22 meshes with the longitudinal groove 20 of the opposing snapping element 19 and the snapping element 19 grips behind the outer edge 23 of the opposing transverse beam 22.

Thus, the latching means formed by the snapping element 19 and the opposing transverse beam 22 latches when the needle cover is transferred from the advanced position to the proximal needle protecting position near or immediately before reaching the needle protecting position. In the latched needle protecting position, the support element 11 together with the needle receptacle 16 is blocked from moving.

However, as long as the spring-elastic bow 18 has not yet been snapped back into its initial position, in order to latch the position of the needle cover, the support element together with the needle receptacle 16 can be retracted back into the advanced position. Since the advanced position is the resting position of the restoring means, restoring forces also act when the support element 11 is retracted into the advanced position.

In the latched needle protecting position (FIG. 3), the side bows 8 are substantially extended longitudinally, but can also run slightly curved, convex or concave. In the latched needle protecting position, the proximal end of the needle is covered by the support element 11 and the needle receptacle 16. As shown in FIG. 3, the proximal end of the needle 2 is completely situated in the bore 17 of the needle receptacle 16. The end of the needle is even prevented from being touched laterally by the cylindrical needle receptacle 16.

The latched needle protecting position can only be released again by simultaneously lifting the spring-elastic bows 18. Since the snapping elements 19 are arranged on diametrically opposing facing sides of the side bows 8, the latching means cannot be unlatched by gripping snapping elements on one and the same side of the needle cover 7, but only by gripping snap elements on opposite sides of the needle cover 7. Therefore, the latching means can be largely prevented from being unintentionally unlatched, such that the danger of injury can be effectively ruled out in the latched needle protecting position. Thus, with the needle cover 7 in the latched needle protecting position, the cannula support 1 can be removed from the injection device or from an adapter and disposed of, without any danger of injury.

In one embodiment, the needle cover is operated as follows: when the latching means is unlatched, the needle receptacle 16 together with the support element 11 can be moved freely back and forth. By placing the support element 11 onto a tissue and exerting a proximally directed pressure force, the injection needle 2 is injected into the tissue. The support element 11 can be maximally retracted up to the retracted position. Once the needle 2 has been removed from the tissue, the needle cover 7 returns to the advanced position shown in FIG. 1 again, due to the restoring forces. This process can be repeated a number of times, such that the injection device can be used a number of times in succession, if desired.

The needle receptacle 16 is proximally advanced further by gripping the side areas 9, 10 of the needle cover 7 and pressing together the same, until the latched needle protecting position is eventually reached, in which the latching means latches and prevents the needle receptacle 16 from being retracted.

FIG. 4 shows another variant of the needle cover in accordance with the invention. In accordance with FIG. 4, the needle cover 7 comprises three telescopic sleeves 24, 25 and 26 which surround the needle 2. Instead of the sleeves, a bellows can also be provided which is connected to the support element 11 and the base plate 12. The side bows 8 and/or other restoring means, for example springs, can serve as restoring means which return the proximal sleeve 24 to the advanced position shown in FIG. 4. In principle, the needle cover 7 can also comprise a different number of telescopic sleeves, such as two sleeves.

Figure 4A:
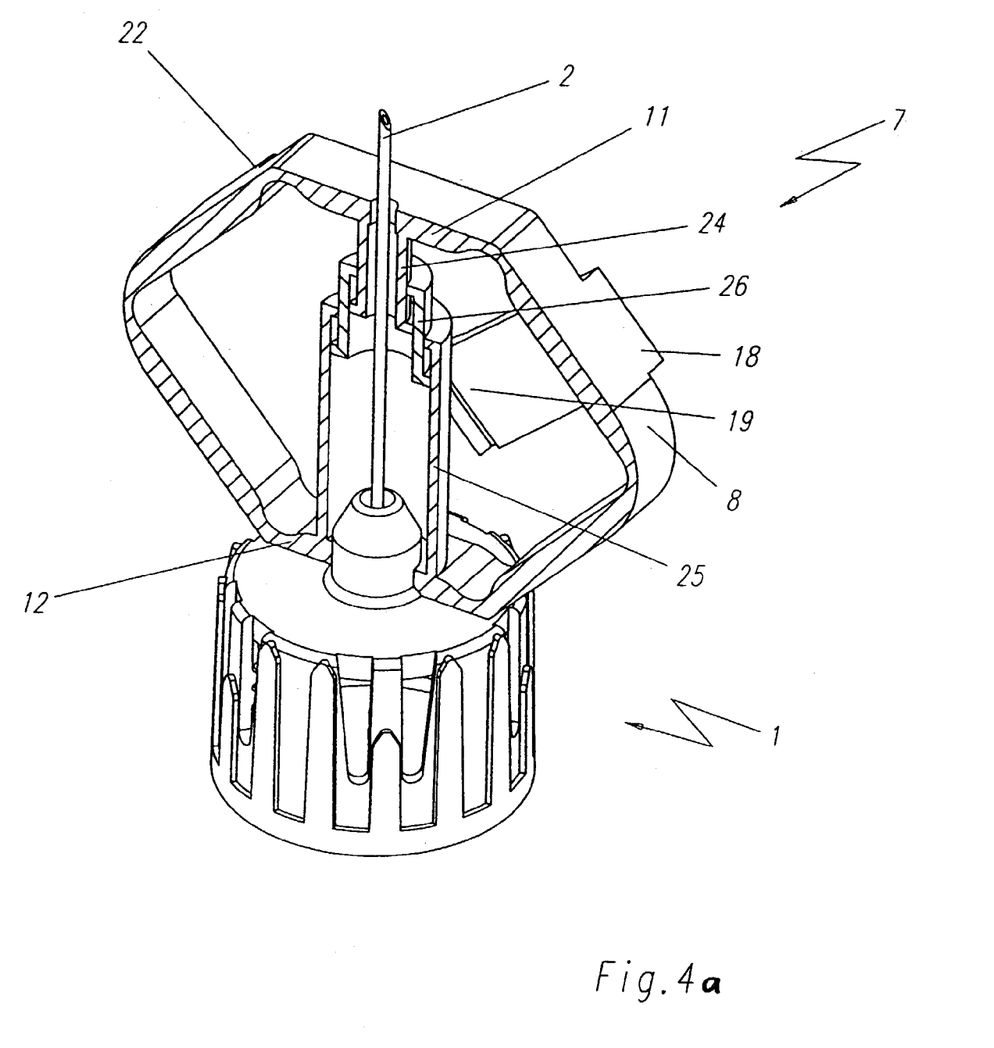
FIGS. 4a–c, depicts a variant of the needle cover in accordance with the present invention, in a resting position, a latched needle protecting position, and a maximally retracted position, each in a partial section.

The needle cover 7 is shown in FIG. 4*a* in the advanced position, in a partial section. This shows how the cylindrical protrusion 24 of the support element 11, said protrusion extending distally inwards, surrounds a front section of the needle 2 and protrudes via a collar into the center sleeve 26 of the telescopic sleeves 24, 25, 26. The sleeve 24 can only be maximally advanced proximally until the collar comes to rest on the base of the center sleeve 26. Correspondingly, the center sleeve 26 can only be proximally advanced until the collar comes to rest on the inner base of the distal sleeve 25.

Figure 4B:
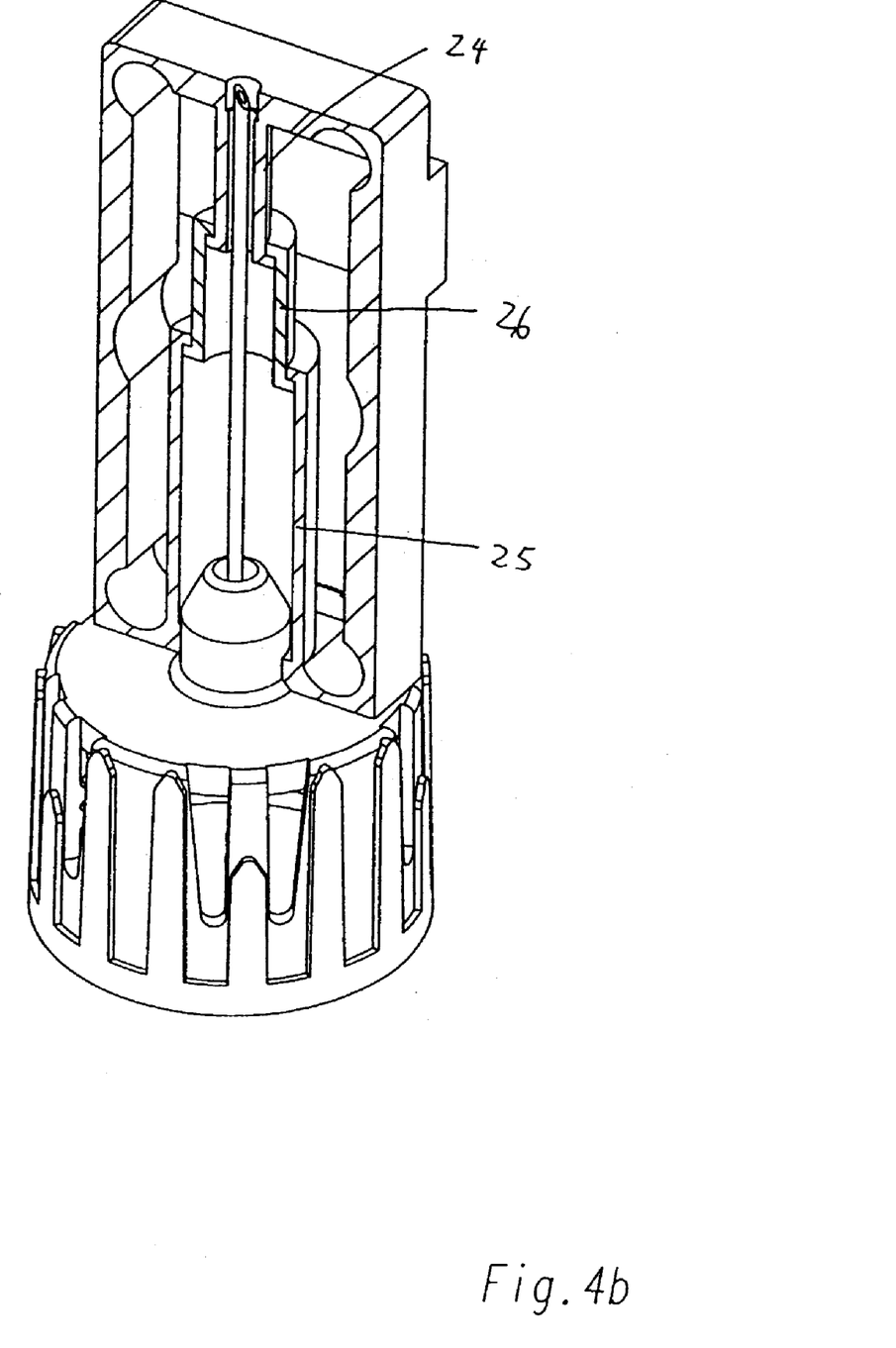
Figure 4C:
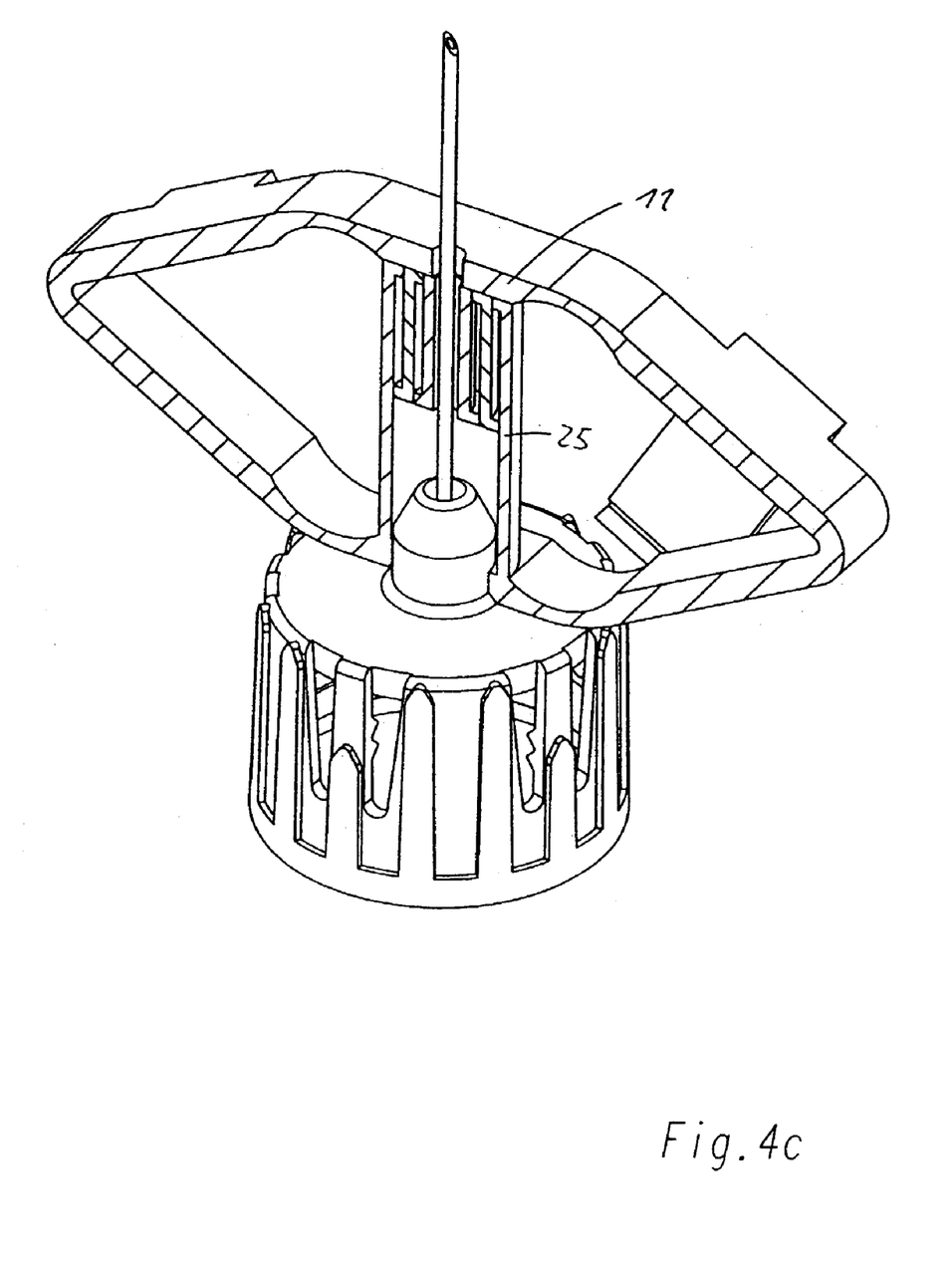

FIG. 4*b* shows the needle cover 7 in its latched needle protecting position in which the collars of each of the sleeves 24 and 26 come to rest on the base of a corresponding outer sleeve, respectively. Lastly, FIG. 4*c* shows the needle cover 7 in its maximally retracted position in which the inner side of the support element 11 comes to rest on the facing side of the distal sleeve 25.

Figure 5:
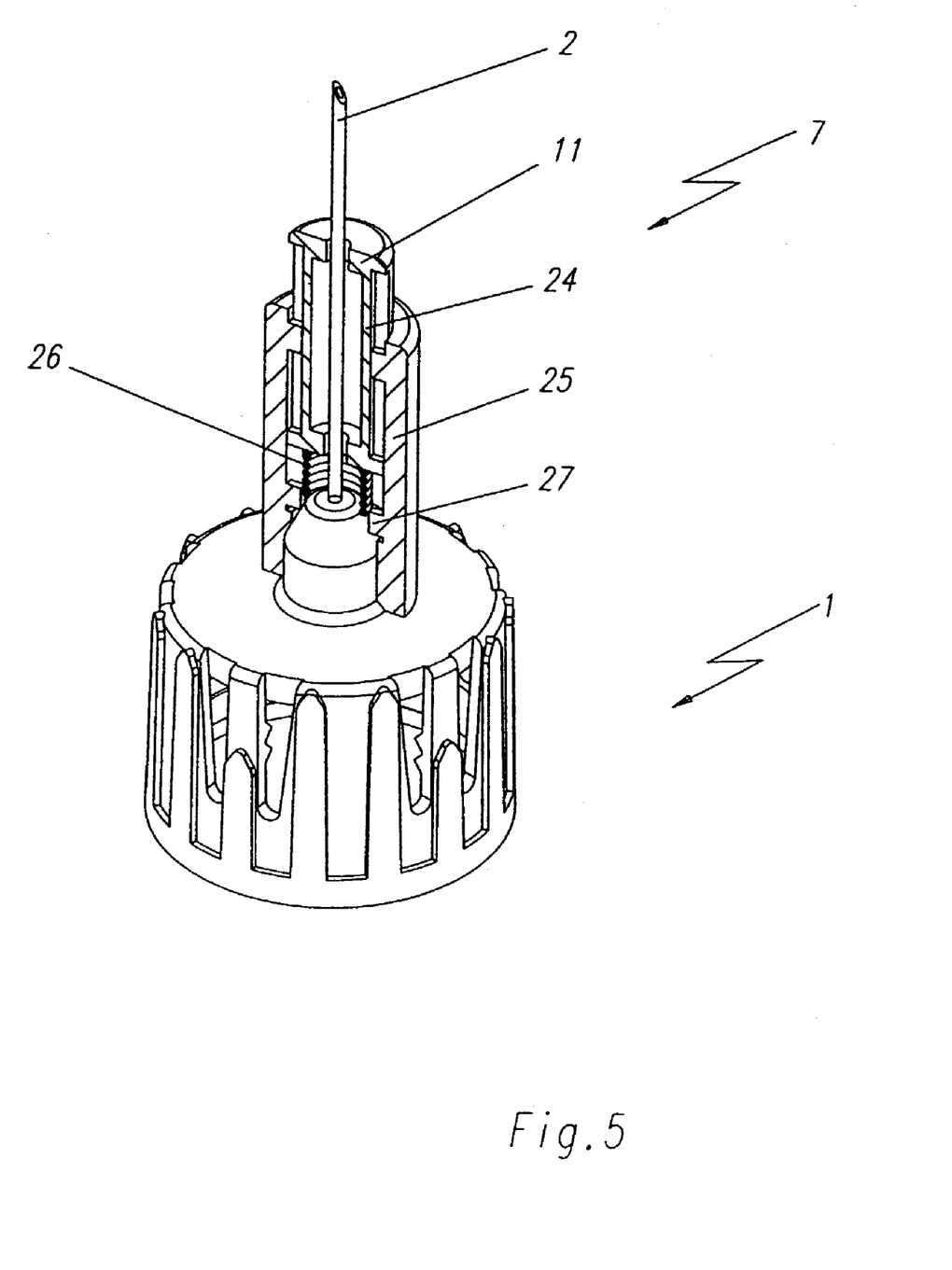
FIG. 5 depicts another embodiment of a needle cover in accordance with the present invention, in a partial section.

FIG. 5 shows a partial section of another embodiment, which does not comprise side bows. In this embodiment, the needle cover 7 includes a distal sleeve 25 and a proximal sleeve 24 which are telescopic and each surround the needle 2. The proximal sleeve 24 can be retracted into the distal sleeve 25. Stopper projections 27 arranged on the inner side of the distal sleeve 25 serve to limit the restoring movement. A spring 26 acting on the proximal sleeve 24 serves as a restoring means for returning the needle cover.

In order to transfer the needle cover to the needle protecting position, the position of the proximal sleeve 24, serving as the covering means, is changed until the support element 11 covers the proximal end of the needle and a latching means latches the needle protecting position. To this end, a coulisse guide can be provided on the inner wall of the distal sleeve 25, with which a pin provided on the outer wall of the proximal sleeve 24 meshes. The coulisse can, for example, be guided in a spiral, wherein the pin locks into a recess of the coulisse guide when the needle protecting position is reached.

Alternatively, hooking means can be provided on the upper circumferential rim of the distal sleeve 25, said hooking means being activated when the proximal sleeve 24 is advanced proximally beyond the advanced position shown in FIG. 5.

The elements of the needle cover 7 are preferably made of plastic, preferably by injection molding or other suitable process. The needle cover 7 shown in FIGS. 1 to 4 is preferably injection-molded in the advanced position, automatically pre-setting the resting position of the needle cover. The needle cover 7 may be detachably or non-detachably operably connected to a cannula support which, in one embodiment, supports a 31-gauge injection needle. One preferred use or application is that of covering an injection needle of an injection pen for administering a medicine, for example insulin or hormone, or another therapeutic or diagnostic fluid.

In order to store the needle cover 7 and/or a cannula support 1 in a sterile condition, it or they can be packaged in a substantially cylindrical or truncated packaging structure comprising a sealing film or blistering. In its stored and/or transport position, the needle cover 7 may preferably be situated in the advanced position in which the latching means are not latched. Side walls 9, 10 of the needle cover 7 then abut side walls of the packaging structure. Once the sealing film has been removed, the injection device, for example an injection pen or an adapter to be placed onto an injection device, can be connected to, e.g., plugged onto, the needle cover 7 and/or the cannula support 1. The needle cover 7 and/or the cannula support 1 can then be removed form the packaging structure. The needle cover 7 then automatically assumes the advanced position.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A needle cover for covering an injection needle of an injection device, including:
   - a covering means, the covering means having an advanced position, a needle protecting position, and a retracted position, the covering means being configured for shifting longitudinally in the axial direction of the needle to the needle protecting position which covers a needle tip end of said needle, the covering means shifting longitudinally along the needle in the axial direction of the needle via a bore surrounding the needle;
   - a restoring means for axially returning said covering means from the retracted position into the advanced position, wherein the restoring means is designed such that a restoring force acts against the covering means advancing from the advanced position into the needle protecting position; and
   - a plurality of sets of releasable latching means for preventing the covering means from being retracted in said needle protecting position, each set of releasable latching means configured to form a latch when said needle covering means axially moves to said needle protecting position, wherein the position of the covering means is different in said advanced position than in the needle protecting position, and said latching means are activated to prevent the covering means from being retracted when the covering means is shifted near to the needle protecting position.

2. The needle cover as set forth in claim 1, wherein said injection device is an injection pen.

3. The needle cover as set forth in claim 1, wherein the resting position of said restoring means is the advanced position.

4. The needle cover as set forth in claim 1, wherein the plurality of sets of releasable latching means are activated when the covering means is advanced near to the needle protecting position.

5. The needle cover as set forth in claim 1, wherein the plurality of sets of releasable latching means are automatically activated when the covering means is advanced into the needle protecting position.

6. The needle cover as set forth in claim 1, wherein the restoring means includes flexible elements which project symmetrically from the covering means and extend substantially in the longitudinal direction of the needle.

7. The needle cover as set forth in claim 6, wherein said flexible elements are curved radially outwards in the advanced position of the needle and can be compressed into the retracted position due to a force acting in the axial direction of the needle.

8. The needle cover as set forth in claim 6, wherein the flexible elements each comprise a weak point in a central region, such that halves of the flexible elements project from said weak point substantially mirror-symmetrically.

9. The needle cover as set forth in claim 6, wherein the plurality of sets of releasable latching means includes spring-elastic elements which each project substantially vertically from facing sides of the flexible elements.

10. The needle cover as set forth in claim 9, wherein the restoring means includes two or four flexible elements, wherein said spring-elastic elements project from diametrically opposing facing sides of the spring-elastic elements.

11. The needle cover as set forth in claim 9, wherein the spring-elastic elements are each formed as a snapping element for gripping behind an edge of an opposing flexible element in the latched needle protecting position.

12. The needle cover as set forth in claim 11, wherein said snapping element comprises a chamfer along which said edge of said opposing flexible element slides when the latching means is latched.

13. The needle cover as set forth in claim 6, wherein the plurality of sets of releasable latching means are arranged in an upper half of the flexible elements.

14. The needle cover as set forth in claim 6, wherein the covering means is coupled to the flexible elements, such that compressing the flexible elements causes the covering means to be shifted longitudinally.

15. The needle cover as set forth in claim 14, wherein the covering means includes a sleeve which surrounds the needle.

16. The needle cover as set forth in claim 15, comprising another sleeve which surrounds the needle, wherein said two sleeves are telescopic.

17. The needle cover as set forth in claim 14, wherein the covering means includes a bellow which surrounds the needle.

18. The needle cover as set forth in claim 1, wherein the covering means includes telescopic sleeves which surround the needle, wherein the plurality of sets of releasable latching means are designed such that said sleeves can be latched by a plurality of latches by being relatively rotated or by being axially shifted relative to each other beyond the advanced position.

19. The needle cover as set forth in claim 18, wherein the plurality of sets of releasable latching means includes a plurality of coulisse guides and pins on a side wall of a sleeve or on a proximal circumferential rim of a distal sleeve which guides the relative rotation, in order to transfer the sleeves to the needle protecting position.

20. The needle cover as set forth in claim 18, wherein the plurality of sets of releasable latching means includes locking element sets which lock into each other when a proximal sleeve is axially shifted into the needle protecting position.

21. The needle cover as set forth in claim 1, wherein a proximal end of the needle proximally protrudes beyond a support area of the needle cover when the covering means is in the advanced position.

22. The needle cover as set forth in claim 1, further comprising a cannula support comprising an injection needle for injecting a fluid, wherein the needle cover is detachably or non-detachably connected to said cannula support.

23. The needle cover as set forth in claim 22, wherein the needle is a 31-gauge needle.

24. A needle cover for covering an injection needle, comprising:
   a cover, the cover having an advanced position, a needle protecting position, and a retracted position, the cover being configured for shifting along the needle to a needle protecting position which covers a needle tip end of said needle, the cover shifting longitudinally along the needle in the axial direction of the needle via a bore surrounding the needle;
   a return mechanism for axially moving said cover from the a retracted position into the advanced position, wherein the return mechanism is designed such that a restoring force acts against the cover advancing from the advanced position into the needle protecting position; and
   a plurality of sets of releasable latches for preventing the cover from being retracted in said needle protecting position, each set of releasable latches configured to form a latch when said cover axially moves to said needle protecting position, wherein the position of the cover is different in said advanced position than in the needle protecting position, and said plurality of sets of releasable latches is activated to prevent the cover from being retracted when the cover is moved near the needle protecting position.

25. The needle cover as set forth in claim 24, wherein the latch is automatically activated when the cover is moved into the needle protecting position.

26. The needle cover as set forth in claim 25, wherein the return mechanism includes flexible elements which project symmetrically from the cover.

27. The needle cover as set forth in claim 26, wherein the plurality of sets of releasable latches include spring-elastic elements which each project from the flexible elements.

28. The needle cover as set forth in claim 24, wherein the cover includes telescopic sleeves which surround the needle, and wherein the plurality of sets of releasable latches are designed such that said sleeves can be latched by being relatively rotated or by being axially shifted relative to each other beyond the advanced position.

29. A needle cover for covering an injection needle, comprising:
   a cover, the cover having an advanced position, a needle protecting position, and a retracted position, the cover being configured for shifting along the needle to a needle protecting position which covers a needle tip end of said needle, the cover shifting longitudinally along the needle in the axial direction of the needle via a bore surrounding the needle;
   a return mechanism for axially moving said cover from the a retracted position into the advanced position, the return mechanism comprising two or four flexible elements that project symmetrically from the cover and extend substantially in the longitudinal direction of the needle and include a weak point in a central region such that halves of the flexible elements project from said weak point substantially mirror-symmetrically, wherein the return mechanism is designed such that a restoring force acts against the cover advancing from the advanced position into the needle protecting position; and a plurality of sets of releasable latches for preventing the cover from being retracted in said needle protecting position, each set of releasable latches including a spring-elastic element and an edge of an opposing flexible element, each spring-elastic element projecting from the flexible element and formed as a snapping element for gripping behind the edge of the opposing flexible element in the latched needle protecting position, wherein the position of the cover is different in said advanced position than in the needle protecting position, and said plurality of sets of releasable latches is activated to prevent the cover from being retracted when the cover is moved near the needle protecting position.

* * * * *

UNITED STATES PATENT AND TRADEMARK OFFICE
CERTIFICATE OF CORRECTION

PATENT NO. : 7,211,069 B2 Page 1 of 1
APPLICATION NO. : 10/358622
DATED : May 1, 2007
INVENTOR(S) : Hans-Ulrich Lehmann

It is certified that error appears in the above-identified patent and that said Letters Patent is hereby corrected as shown below:

Claims:

| Col. | Line | PTO | Should Read |
|---|---|---|---|
| 10 | 25 | "the a retracted" | -- the retracted -- |
| 10 | 65 | "the a retracted" | -- the retracted -- |

Signed and Sealed this

Seventh Day of August, 2007

JON W. DUDAS
*Director of the United States Patent and Trademark Office*